(12) United States Patent
Daizade

(10) Patent No.: US 8,083,703 B2
(45) Date of Patent: Dec. 27, 2011

(54) CLUBFOOT ORTHOTICS

(75) Inventor: Izak Daizade, Herzelia Pituach (IL)

(73) Assignee: Izak Daizade, Herzelia Pituach (IL)

( * ) Notice: Subject to any disclaimer, the term of this patent is extended or adjusted under 35 U.S.C. 154(b) by 418 days.

(21) Appl. No.: 12/323,784

(22) Filed: Nov. 26, 2008

(65) Prior Publication Data

US 2009/0076429 A1    Mar. 19, 2009

Related U.S. Application Data

(63) Continuation-in-part of application No. PCT/IL2008/000978, filed on Jul. 15, 2008.

(60) Provisional application No. 61/107,733, filed on Oct. 23, 2008.

(30) Foreign Application Priority Data

Jul. 24, 2007 (IL) .......................................... 184812

(51) Int. Cl.
*A61F 5/00* (2006.01)

(52) U.S. Cl. .......................................... 602/23; 602/29

(58) Field of Classification Search ............... 602/23–27; 128/882
See application file for complete search history.

(56) References Cited

U.S. PATENT DOCUMENTS

| 114,669 | A | * | 5/1871 | Emory | 602/29 |
| 1,691,235 | A | * | 11/1928 | Fischer | 602/29 |
| 3,308,829 | A | | 3/1967 | Edwards | |
| 4,817,589 | A | * | 4/1989 | Wertz | 602/28 |
| 4,922,895 | A | | 5/1990 | Chong | |
| 4,981,132 | A | | 1/1991 | Chong | |
| 5,277,699 | A | | 1/1994 | Williamson | |
| 5,376,068 | A | * | 12/1994 | Grifka | 602/27 |
| 5,593,383 | A | * | 1/1997 | DeToro | 602/27 |

FOREIGN PATENT DOCUMENTS

EP    0 130 915    1/1985

* cited by examiner

*Primary Examiner* — Michael A. Brown
(74) *Attorney, Agent, or Firm* — The Law Office of Michael E. Kondoudis

(57) ABSTRACT

Disclosed is an orthotic for treating at least one component of talipes equinovarus. The orthotic includes an orthotic shell having a plantar support surface configured to support a portion of a foot disposed in the orthotic. The plantar support surface includes a cutout extending laterally through at least a portion of a midfoot portion, and a posterior cuboid supporting surface having a medial boundary, at least a portion of the medial boundary being defined by at least a portion of the cutout.

12 Claims, 15 Drawing Sheets

CLUBFOOT ORTHOTICS

CROSS REFERENCE TO RELATED APPLICATIONS

This application is a Continuation in Part claiming the benefit of PCT international application No. PCT/IL/2008/000978, filed Jul. 15, 2008, which, in turn, claimed the benefit of IL Application No. 184812, filed Jul. 24, 2007, where the content of both aforementioned applications is incorporated by reference as if fully set forth herein. In addition, this application further claims the benefit of Provisional Patent Application No. 61/107,733, filed Oct. 23, 2008, the content of which is incorporated by reference herein in its entirety.

FIELD AND BACKGROUND OF THE INVENTION

The present invention, in some embodiments thereof, relates to orthotic devices that aid in the correction of one or more components of congenital idiopathic talipes equinovarus, and, more particularly, but not exclusively, to methods for applying said orthotic device to achieve the correction.

Congenital idiopathic talipes equinovarus, herein clubfoot deformity or talipes equinovarus, is a complex deformity that occurs in otherwise generally healthy infants and includes equinus of the rearfoot, varus of the calcaneus, adductus of the forefoot, and forefoot supinatus, which must be treated in the infant.

If left untreated, clubfoot deformity will result in secondary bony changes wherein the adult walks on the lateral aspect, instead of the plantar aspect, of the foot; often with a severely deformed gait pattern.

Conservative treatment of clubfoot deformity is known to be preferable to surgical correction. In 1950, Ignacio Ponseti, MD, at the University of Iowa, developed a conservative method for treating clubfoot using straight-last shoes positioned in abduction and connected to a transverse bar.

Additional background art includes U.S. Pat. No. 4,922,895 (Chong), the content of which is incorporated by reference as if fully set forth herein.

SUMMARY OF THE INVENTION

According to an aspect of some embodiments of the invention, there is provided an orthotic for treating at least one component of talipes equinovarus. The orthotic includes an orthotic shell having a plantar support surface configured to support a portion of a foot disposed in the orthotic. The plantar support surface includes a cutout extending laterally through at least a portion of a midfoot portion, and a posterior cuboid supporting surface having a medial boundary, at least a portion of the medial boundary being defined by at least a portion of the cutout.

In some embodiments of the invention, the orthotic includes a wall configured to surround: a medial boundary of the foot, and a heel portion of the foot.

In some embodiments of the invention, the orthotic includes a strap having one end attached to a midfoot portion of the wall surrounding the medial boundary and having a length configured to pass substantially dorsally over the foot, plantigrade through at least a portion of the cutout in the orthotic shell.

In some embodiments of the invention, the length of the strap is additionally configured to pass through a retainer located on a medial side of the medial wall.

In some embodiments of the invention, the length of the strap is additionally configured to extend laterally over a plantar aspect of the plantar orthotic In some embodiments of the invention, the length of the strap is additionally configured to extend dorsally over the orthotic from the plantar aspect.

In some embodiments of the invention, the orthotic includes a strap affixer that affixes the strap in position.

In some embodiments of the invention, the orthotic includes a stretchable band such that when the foot is disposed in the orthotic, the stretchable band extends from a below knee portion of a leg associated with the foot to an anterior portion of the orthotic.

In some embodiments of the invention, the stretchable band is configured to dorsiflex an anterior portion of the orthotic and thereby reduces an equinus deformity when the foot is positioned in the orthotic.

In some embodiments of the invention, the stretchable band includes a leg affixator configured affix one end of the stretchable band over a portion of the leg.

In some embodiments of the invention, the tension exerted on the anterior portion of the orthotic by the stretchable band is adjustable.

In some embodiments of the invention, the orthotic includes an elongate Achilles support extending from a posterior aspect of the orthotic and configured to extend along the posterior aspect of the leg.

In some embodiments of the invention, the strap is of a sufficient length to additionally pass around the elongate Achilles support.

In some embodiments of the invention, the orthotic includes a strap retainer that retains the strap in position around the elongate Achilles support.

In some embodiments of the invention, the orthotic includes padding on a plantar surface of a dorsal of the strap, the padding configured, when the foot is disposed in the orthotic, to contact at least a portion of at least one of: a rearfoot, and a midfoot.

In some embodiments of the invention, the orthotic includes a first ray flange extending from at least a portion of the wall configured to surround a medial boundary of the foot.

In some embodiments of the invention, the orthotic includes padding along a portion of the medial boundary of the foot, and the heel of the foot.

According to another aspect of some embodiments of the invention, there is provided an orthotic for treating at least one component of talipes equinovarus. The orthotic includes a wall configured to extend substantially vertically against a medial boundary of a forefoot, a medial boundary of a midfoot, and around a medial, a posterior, and a lateral boundary of a heel when the foot is placed in the orthotic.

The orthotic additionally includes a substantially planar rearfoot supporting surface extending from a lower boundary between the medial, the posterior, and the lateral boundary of the heel; a substantially planar posterior cuboid supporting surface extending substantially laterally from a lower boundary of the wall along the midfoot, the posterior cuboid supporting surface having a lateral boundary operatively associated with a posterior portion of a cuboid when the foot is disposed in the orthotic; a substantially planar forefoot supporting surface extending substantially laterally from a lower boundary of the wall along the medial boundary of the forefoot; and a strap configured to encircle a midfoot of the foot when the foot is disposed in the orthotic, the strap being further configured to pass between the forefoot supporting surface and the rearfoot supporting surface, and proximate to the lateral boundary of the posterior cuboid supporting surface.

In some embodiments of the invention, the orthotic includes an elongate Achilles support extending from a posterior aspect of the orthotic and configured to extend along the posterior aspect of the leg.

In some embodiments of the invention, the elongate Achilles support is flexible.

In some embodiments of the invention, the strap is of a sufficient length to additionally pass around the elongate Achilles support.

In some embodiments of the invention, the strap is stretchable.

In some embodiments of the invention, the strap is further configured, when the foot is positioned in the orthotic, to press at least a portion of the posterior cuboid toward at least one of: the posterior cuboid supporting surface, and the wall along a medial boundary of a midfoot.

In some embodiments of the invention, the strap is further configured, when the foot is disposed in the orthotic, to press an anterior portion of a calcaneus plantigrade with respect to the posterior cuboid supporting surface.

In some embodiments of the invention, the strap is padded.

In some embodiments of the invention, the strap is further configured, when the foot is disposed in the orthotic, to reduce a varus deformity in a calcaneus connected to the posterior cuboid.

According to still another aspect of some embodiments of the invention, there is provided an orthotic for treating at least one component of talipes equinovarus, the orthotic including: an orthotic shell configured to surround at least a portion of a foot disposed in the orthotic, the surrounded portion including a plantar support surface and a medial wall extending therefrom and surrounding at least a portion of a medial boundary of the foot; a first ray flange extending from at least a portion of the medial wall, the first ray flange positioned a distance from said plantar support surface, configured to maintain the first ray against the plantar support surface; and an elongate Achilles support extending from a posterior aspect of the orthotic and configured to extend along the posterior aspect of the leg.

In some embodiments of the invention, the orthotic includes a cutout in the orthotic extending laterally through a midfoot portion of the plantar support surface; and a posterior cuboid plantar supporting surface having a medial plantar boundary defined by at least a portion of the cutout.

In some embodiments of the invention the orthotic includes a strap passing around the medial wall and plantarly through the cutout.

In some embodiments of the invention the strap is configured to pull at least one midfoot structure medially and inferiorly while the strap is in the anchored position.

The present invention, in some embodiments thereof, relates to orthotic devices that aid in the correction of one or more components of congenital idiopathic talipes equinovarus, and, more particularly, but not exclusively, to methods for applying said orthotic device to achieve the correction.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques, and procedures for accomplishing a given task including, but not limited to, those manners, means, techniques, and procedures either known to, or readily developed from known manners, means, techniques, and procedures by practitioners of orthopedic biomechanics.

BRIEF DESCRIPTION OF THE DRAWINGS

The present invention, in some embodiments thereof, relates to orthotic devices that aid in the correction of one or more components of congenital idiopathic talipes equinovarus, and, more particularly, but not exclusively, to methods for applying said orthotic device to achieve the correction.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 shows a dorsal view of the bones of a normal right foot;

FIG. 2 shows a dorsal view of the bones of a right clubfoot;

FIG. 3 shows a side view of the bones of a right clubfoot;

FIG. 4 shows a right foot exhibiting forefoot adductus and a known brace used for correcting forefoot adductus;

FIG. 5 shows a right clubfoot being set in a clubfoot orthotic, according to embodiments of the invention;

FIG. 6 shows a dorsal view of the bones of the right clubfoot and clubfoot orthotic of FIG. 5, according to embodiments of the invention;

FIGS. 7-10 show a right clubfoot being strapped into the clubfoot orthotic of FIGS. 5 and 6, according to embodiments of the invention;

FIG. 11 shows a midfoot cutaway view from the anterior of a clubfoot secured in a partial schematic view of the clubfoot orthotic shown in FIG. 5, according to embodiments of the invention;

FIG. 12 shows a dorsal view of the bones of the right clubfoot secured in a partial view of the clubfoot orthotic of FIG. 5, according to embodiments of the invention;

FIG. 13 shows a side view of the clubfoot and clubfoot orthotic of FIG. 5, including an equinus corrector, according to embodiments of the invention;

FIG. 14 shows a right clubfoot being strapped into a clubfoot orthotic having an equinus heel cup, according to embodiments of the invention; and FIG. 15 shows the right clubfoot secured by the clubfoot orthotic of FIG. 14, according to embodiments of the invention.

DETAILED DESCRIPTION OF SOME EMBODIMENTS OF THE INVENTION

Figure 1:
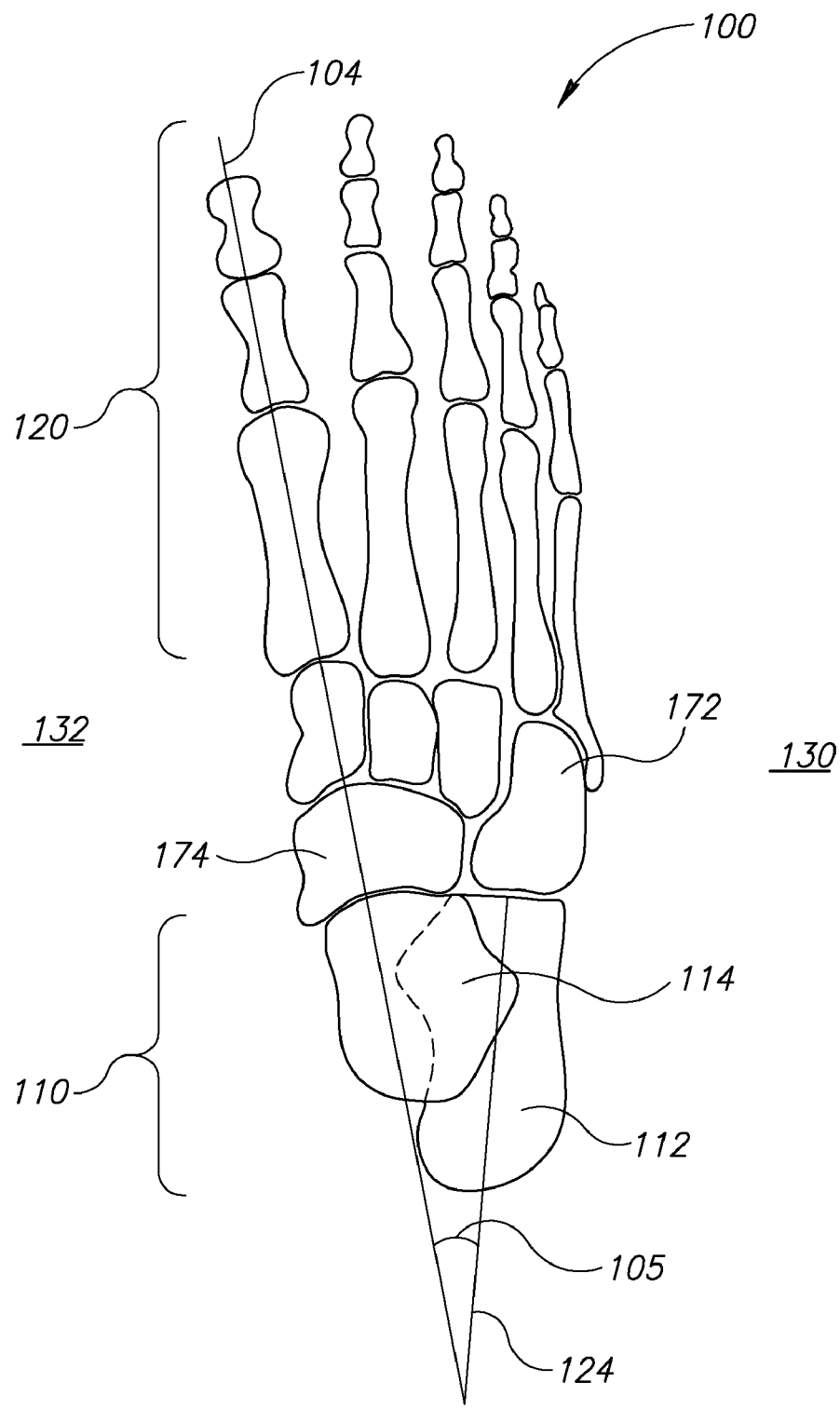

The present invention, in some embodiments thereof, relates to orthotic devices that aid in the correction of one or more components of congenital idiopathic talipes equinovarus, and, more particularly, but not exclusively, to methods for applying said orthotic device to achieve the correction.

The principles and operation of the orthotic devices according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. Further, it is to be understood that the invention is not limited in its application to the details set forth in the following description.

The invention is capable of other embodiments or of being practiced or carried out in various ways. Also, it is to be understood that the phraseology and terminology employed herein is for the purpose of description and should not be regarded as limiting.

Referring now to the drawings:

Club Foot

FIG. 1 shows the bones of a normal right foot 100 from a dorsal view. In a rear foot 110, a calcaneal axis 124 passing through a calcaneus 112 is substantially aligned with a first ray axis 104 passing through a forefoot 120.

Figure 2:
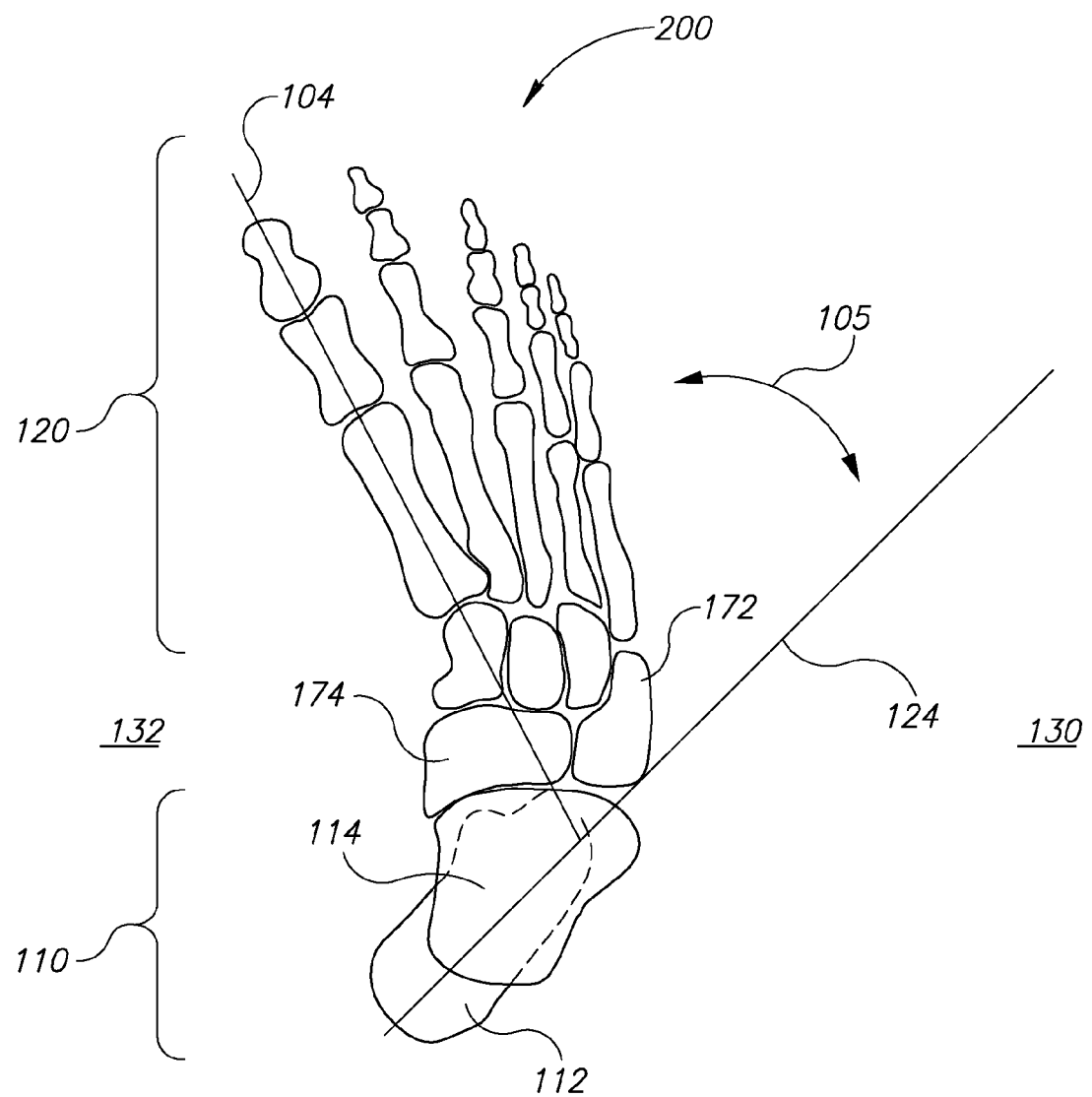

FIG. 2 shows a right clubfoot 200 from an aerial, herein dorsal, view of the foot. Forefoot 120 has moved medially 130, a position herein referred to as a forefoot adductus.

Figure 3:
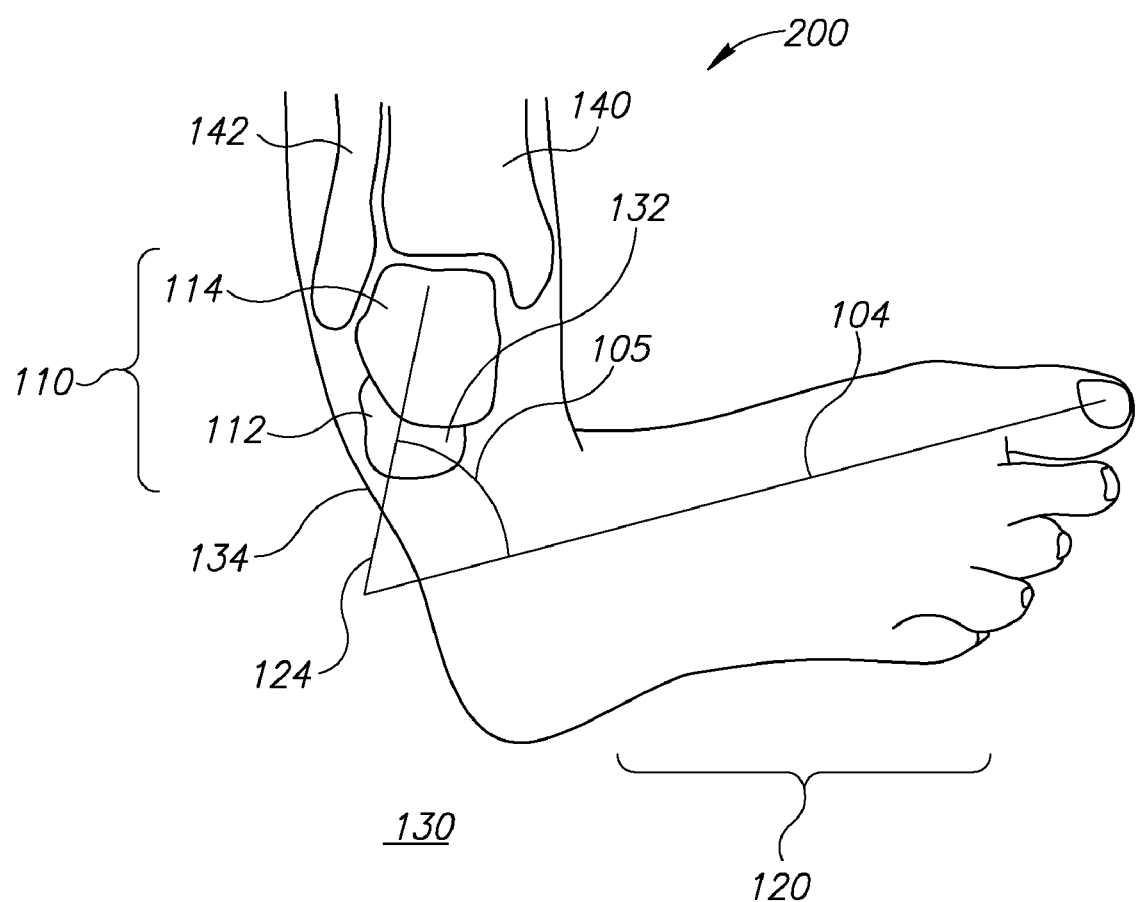

FIG. 3 shows right clubfoot 200 from a side view, demonstrating that rearfoot 110 is turned in and calcaneus 112 has moved under a talus 114 so that calcaneus 112 is rotated and presses an adjacent foot border 134 against the floor; a condition herein referred to as a calcaneal varus. Additionally, forefoot 120 is tilted with first ray axis 104 in the air.

Existing Club Foot Brace

Figure 4:
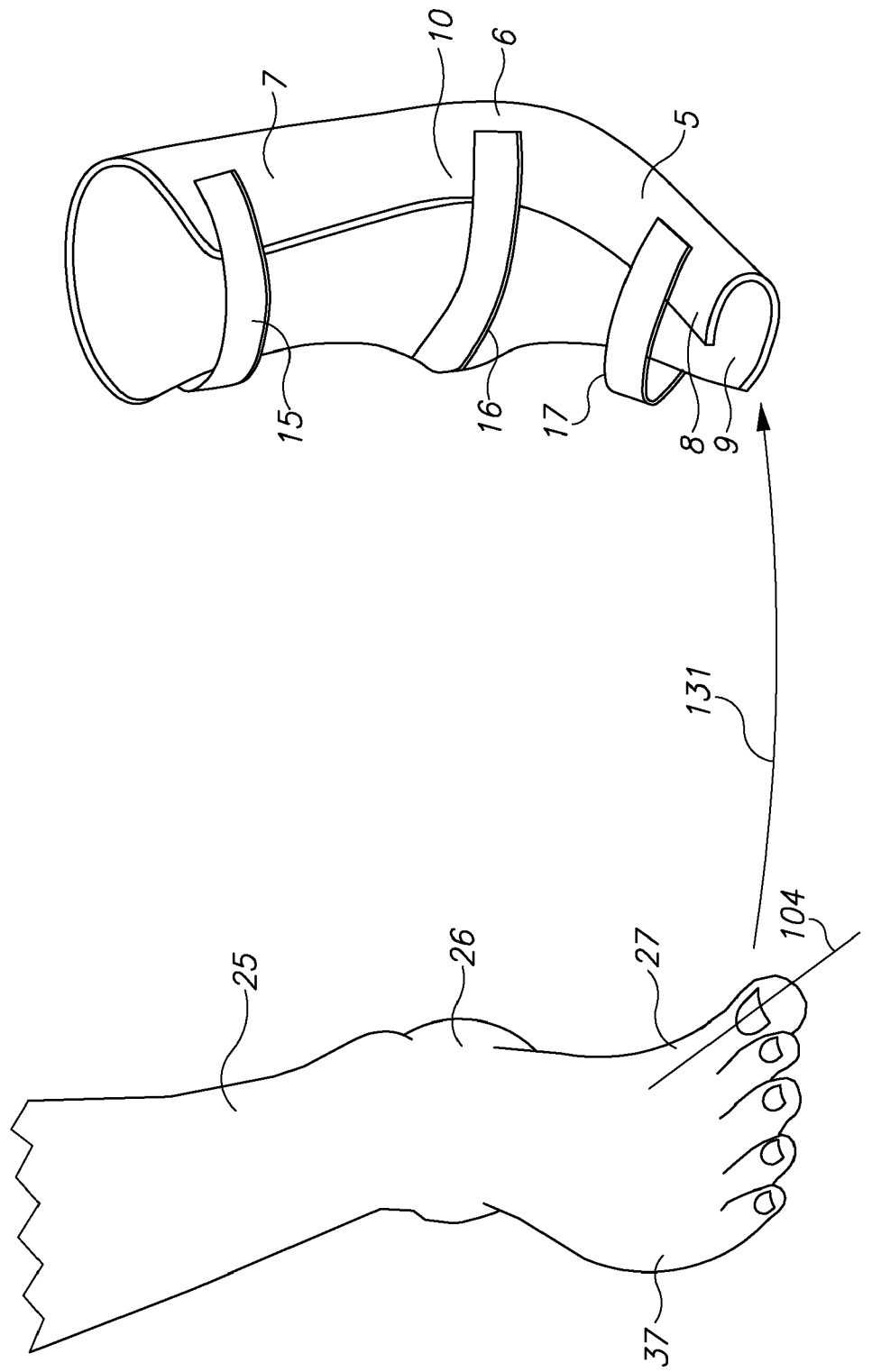

U.S. Pat. No. 4,922,895 (Chong), the contents of which is incorporated by reference as if fully set forth herein, teaches a stand-alone brace 10, shown in FIG. 4, for correction of a foot 210 having an adductus deformity 27 of a forefoot 37.

Brace 10 includes a leg strap 15 that presses a leg 25 in a direction 131 into a leg support 7; a heel strap 16 that pushes a heel 26 into a heel support 6; and a forefoot strap 17 that pushes forefoot 37 into a forefoot support 9, with first ray 104 under a first ray flange 8.

Talipes Equinovarus Orthotic

Figure 5:
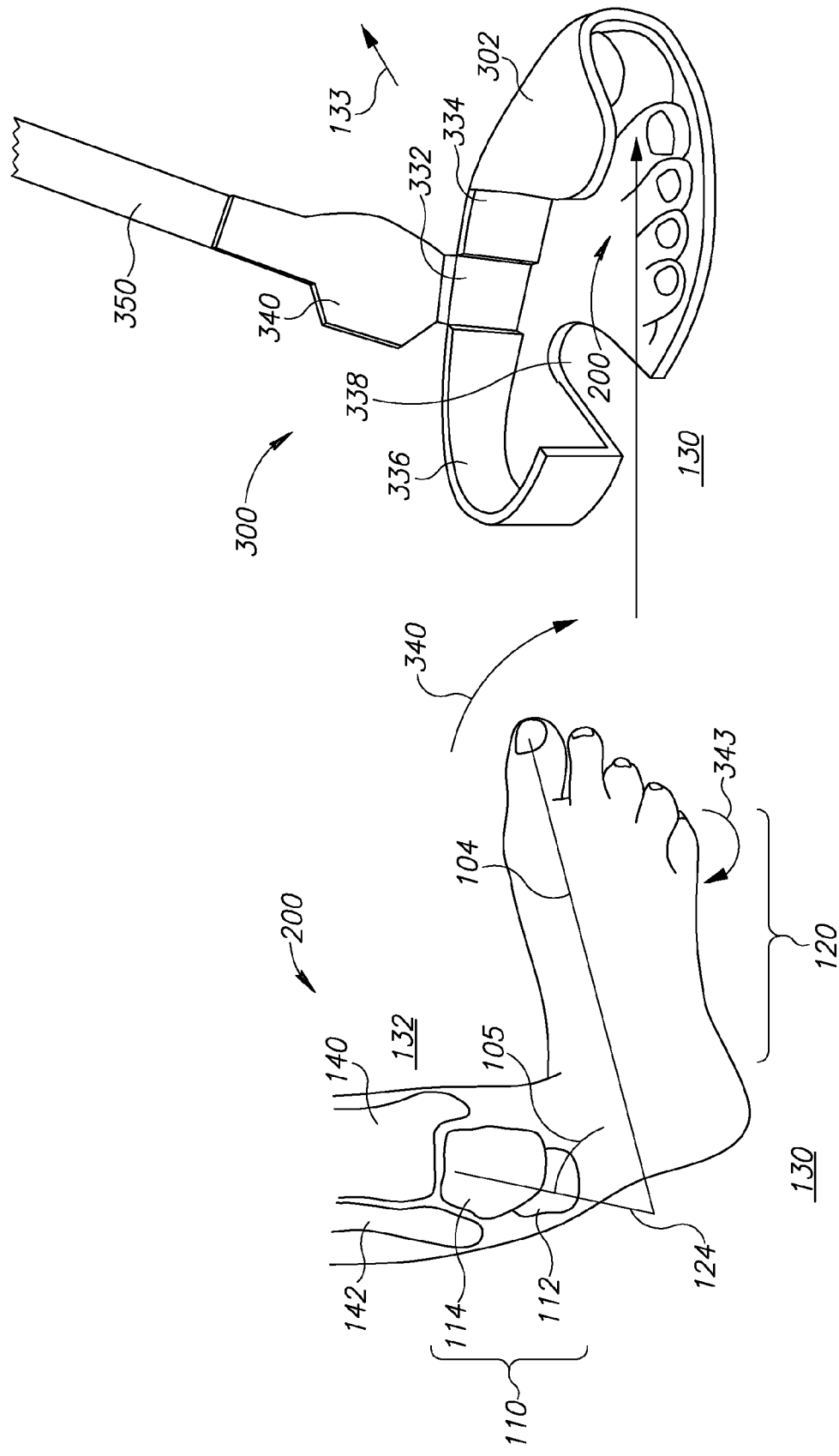

FIG. 5 shows right clubfoot 200 being set in a clubfoot orthotic 300, according to embodiments of the invention.

The ankle joint includes talus 114 that is stabilized between a tibia 140 and a fibula 142. Below talus 114 is calcaneus 112 that is in a varus position.

An abnormally large angle 105 is formed by first ray 104 and calcaneal axis 124. Reduction of angle 105 is initially addressed in restoring proper foot architecture.

Initially, right clubfoot 200 is massaged and forefoot 120 circumducted in a direction 343 while first ray 104 is rotated in plantigrade direction 343 to bring forefoot 120 to a plantigrade position. First ray is then moved in medial direction 133 and clubfoot 200 is manipulated so that first ray 104 sets beneath a first ray flange 302 of clubfoot orthotic 300.

As used herein, the term "orthotic" refers to a support, brace, or splint used to support, align, prevent, or correct the function of movable parts of the body. (Webster's New World™ Medical Dictionary, 3rd Edition)

Figure 6:
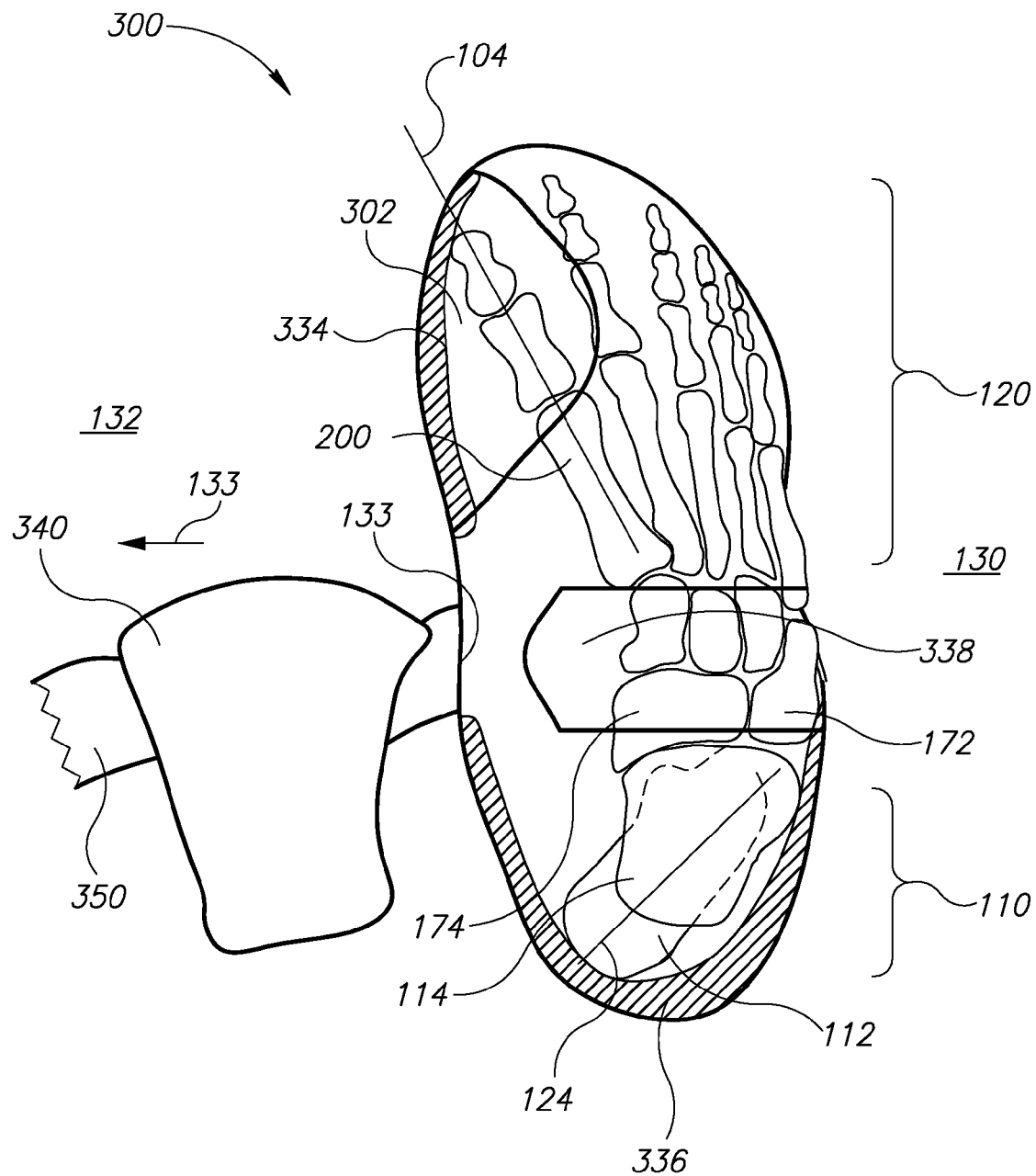

As shown in FIG. 6 in a dorsal view of the bones of clubfoot 200, the supinatus of first ray 104 has come to a plantigrade position and calcaneus 112 is sitting in a padded heel cup 336. Calcaneus 112, however, remains in varus and forefoot 120 still maintains a certain amount of adductus, away from clubfoot orthotic in medial direction 133.

To correct the varus position of calcaneus 112, a posterior cuboid strap 350 is pulled anterior to rearfoot 110, plantarly to a posterior portion of a cuboid 172 and a navicular bone 174 into a subtalar sulcus 338. This causes posterior portion of cuboid 172 to move in medial direction 133. The anterior portion of calcaneus 112 follows the movement of cuboid 172 and presses toward a medial midtarsal depression 332.

Medial midtarsal depression 332 is formed by an unpadded section of clubfoot orthotic 300 between a first ray padding 334 and padded heel cup 336. Pressing calcaneus 112 and posterior portion of cuboid 172 into medial midtarsal depression 332 causes the anterior portion of calcaneus 112 to rotate out of calcaneal varus.

Figure 7:
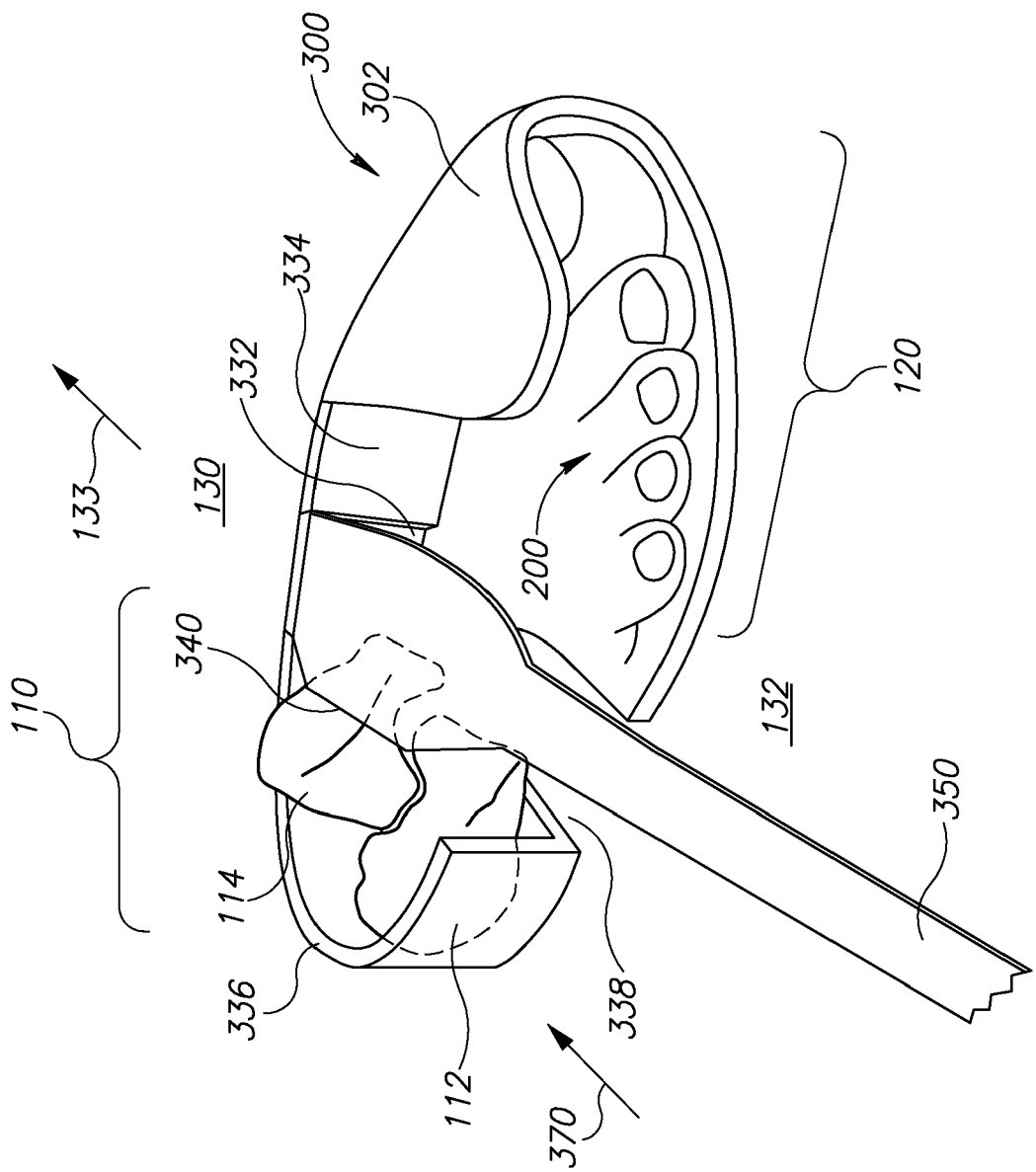

As shown in FIG. 7, posterior cuboid strap 350 has been pulled across clubfoot anterior to rearfoot 110 and plantarly into subtalar sulcus 338 so the anterior portion of calcaneus 112 is pressed into medial midtarsal depression 332 in medial direction 133.

Figure 8:
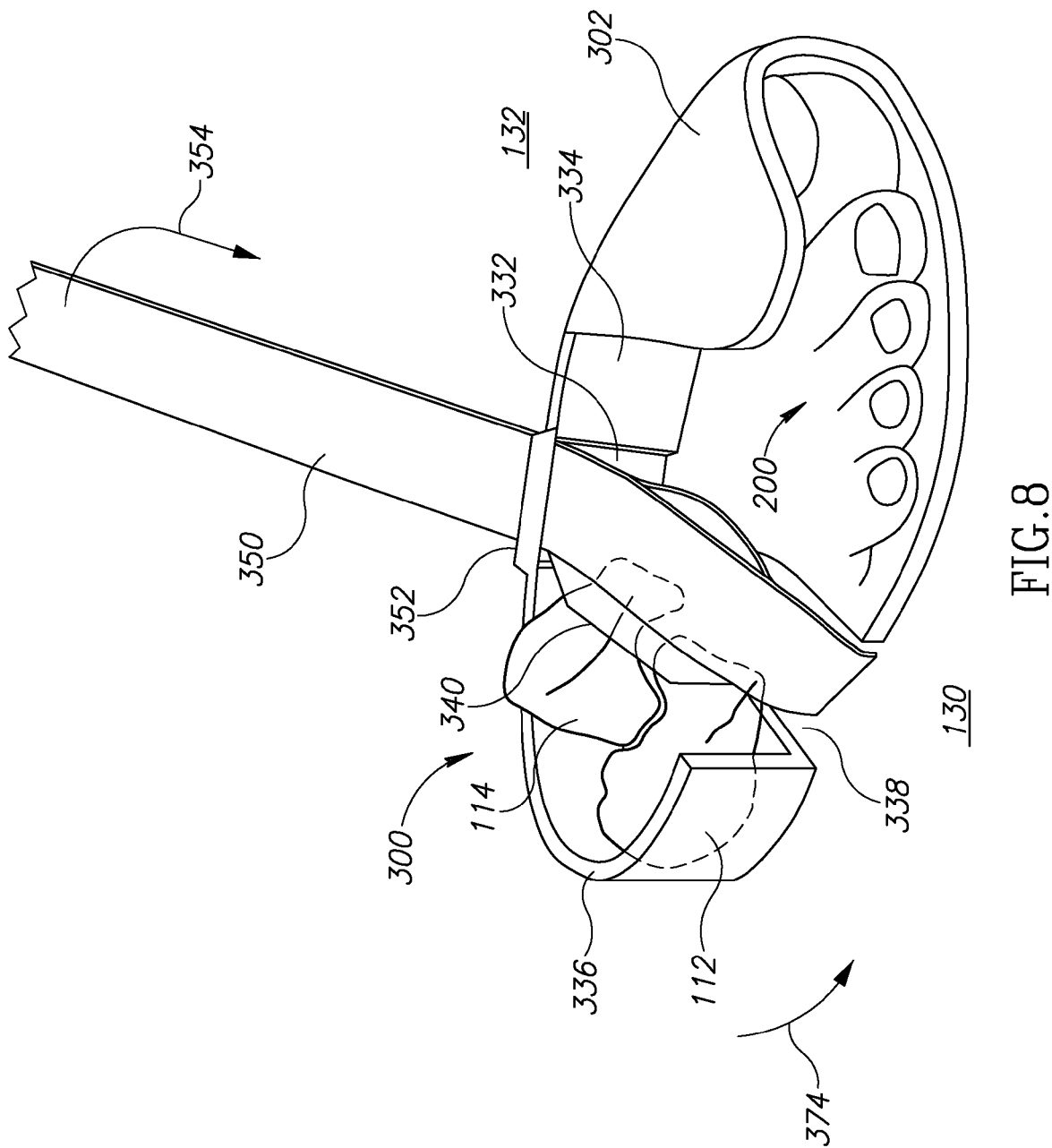

As seen in FIG. 8, posterior cuboid strap 350 has been passed through a clasp 352 that is attached to a medial aspect 132 of clubfoot orthotic 300. Posterior cuboid strap 350 is then pulled taut in a plantigrade direction 354 so that a talar pad 340 presses talus 114 in a plantigrade rotational direction 374, causing calcaneus 112 to stabilize within padded heel cup 336.

Figure 9:
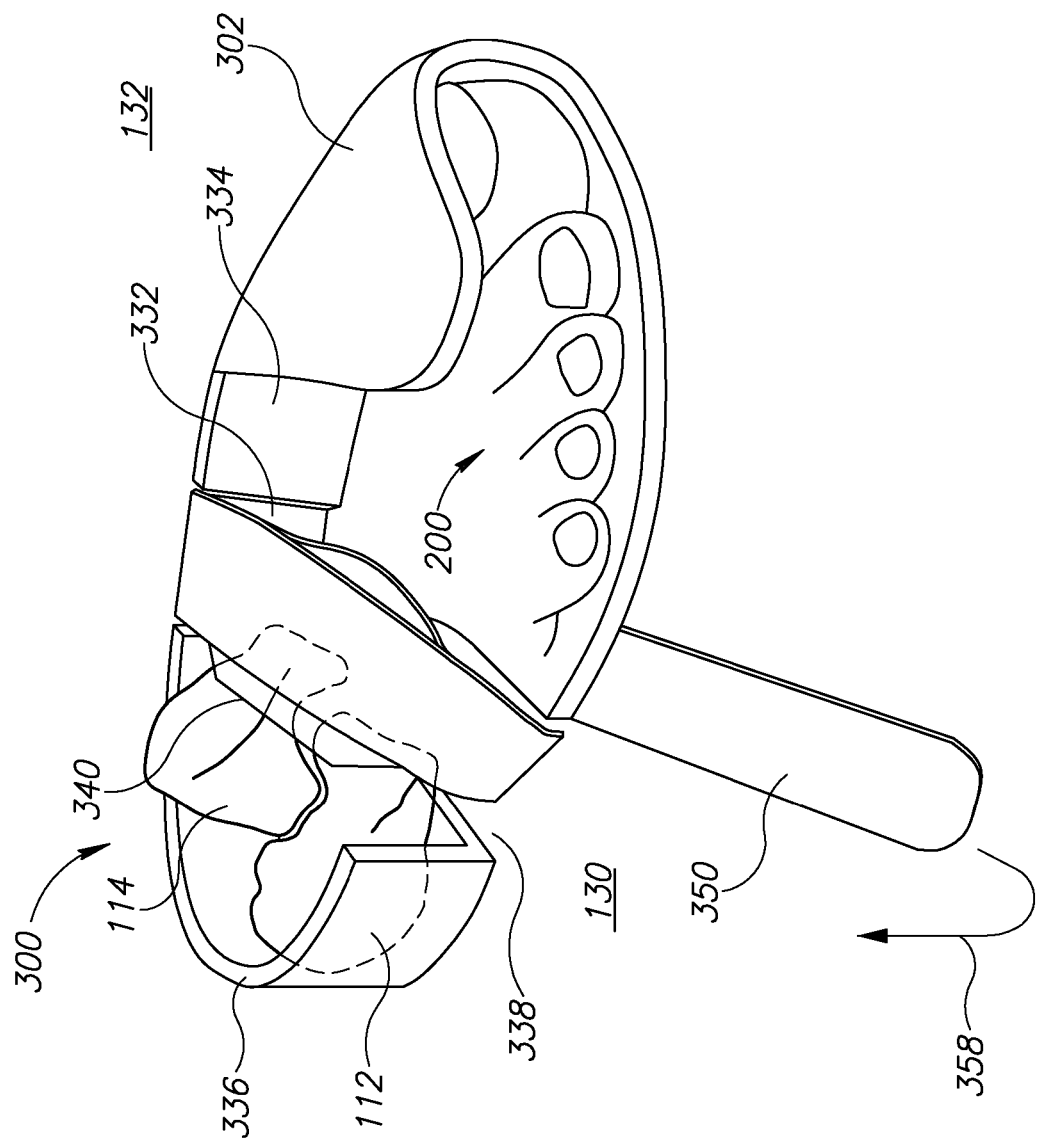
Figure 10:
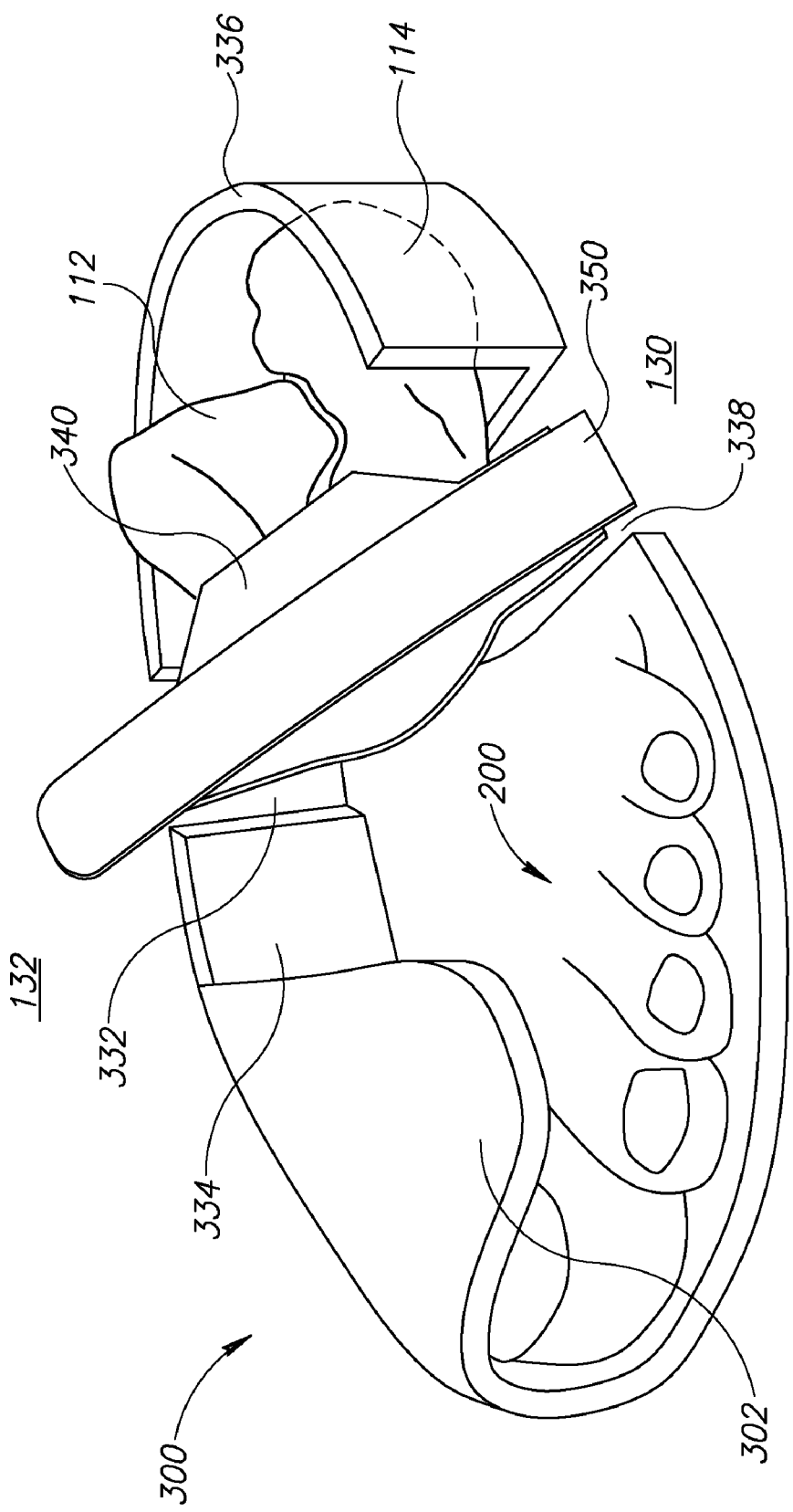

FIG. 9 shows posterior cuboid strap 350 brought across the plantar aspect of clubfoot orthotic 300 and rotated in a dorsal direction 358. As seen in FIG. 10, posterior cuboid strap 350 has been folded dorsally over talar pad 340 in a direction 358.

Figure 11:
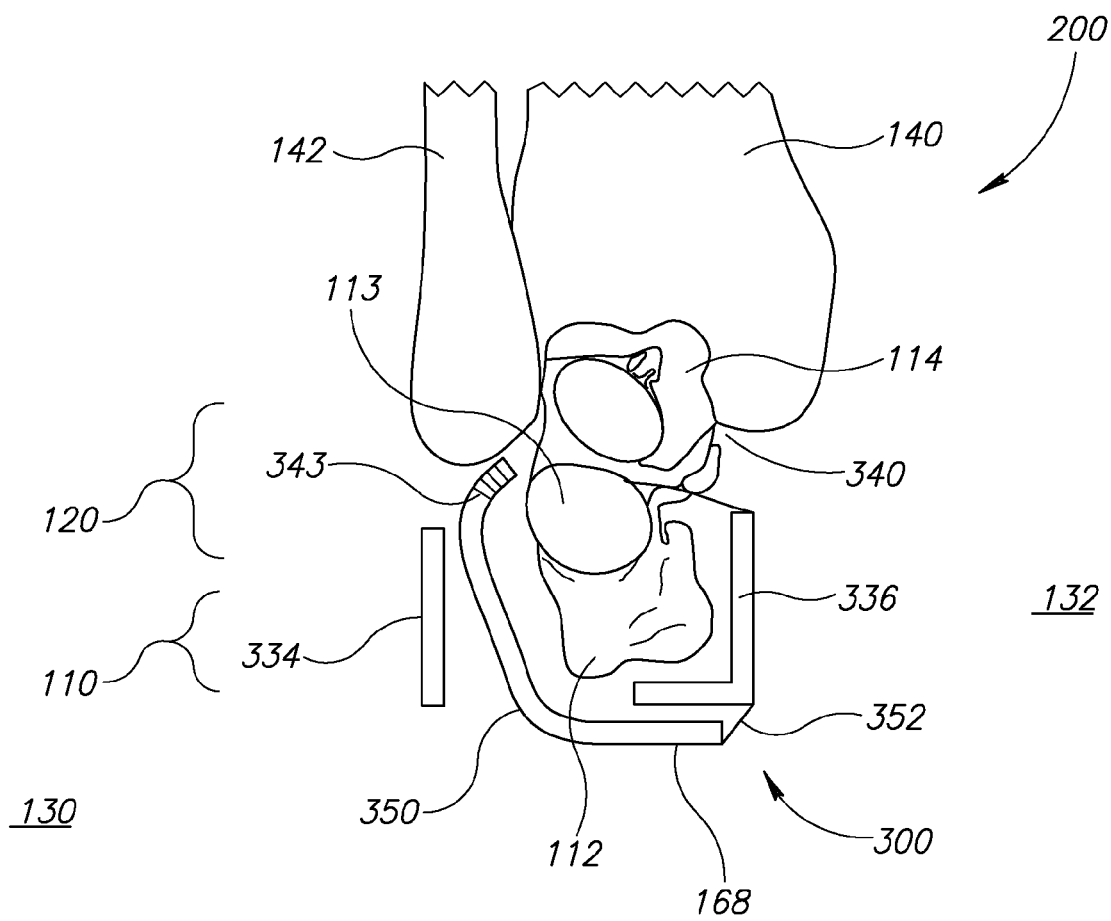

FIG. 11 shows a schematic head-on view of clubfoot orthotic 300 cutaway of clubfoot 200 in which posterior cuboid strap 350 is shown beginning at medial aspect of padded heel cup 336 and pressing a calcaneal head 113 toward a plantar aspect 168 of clubfoot orthotic 300.

Posterior cuboid strap 350 continues below plantar aspect 168, through clasp 352, alternatively referred to as a retainer 352, and doubles back dorsally where posterior cuboid strap 350 is affixed, herein retained in position, for example with Velcro 343.

Alternatively, posterior cuboid strap 350 is optionally retained in position with snaps or clasps, not shown; the many options for retaining the position of posterior cuboid strap 350 being well known to those familiar with the art. The head-on view of calcaneus 112 and talus 114 demonstrate that clubfoot orthotic 300 has achieved a corrected position of calcaneus 112 in the coronal plane.

Figure 12:
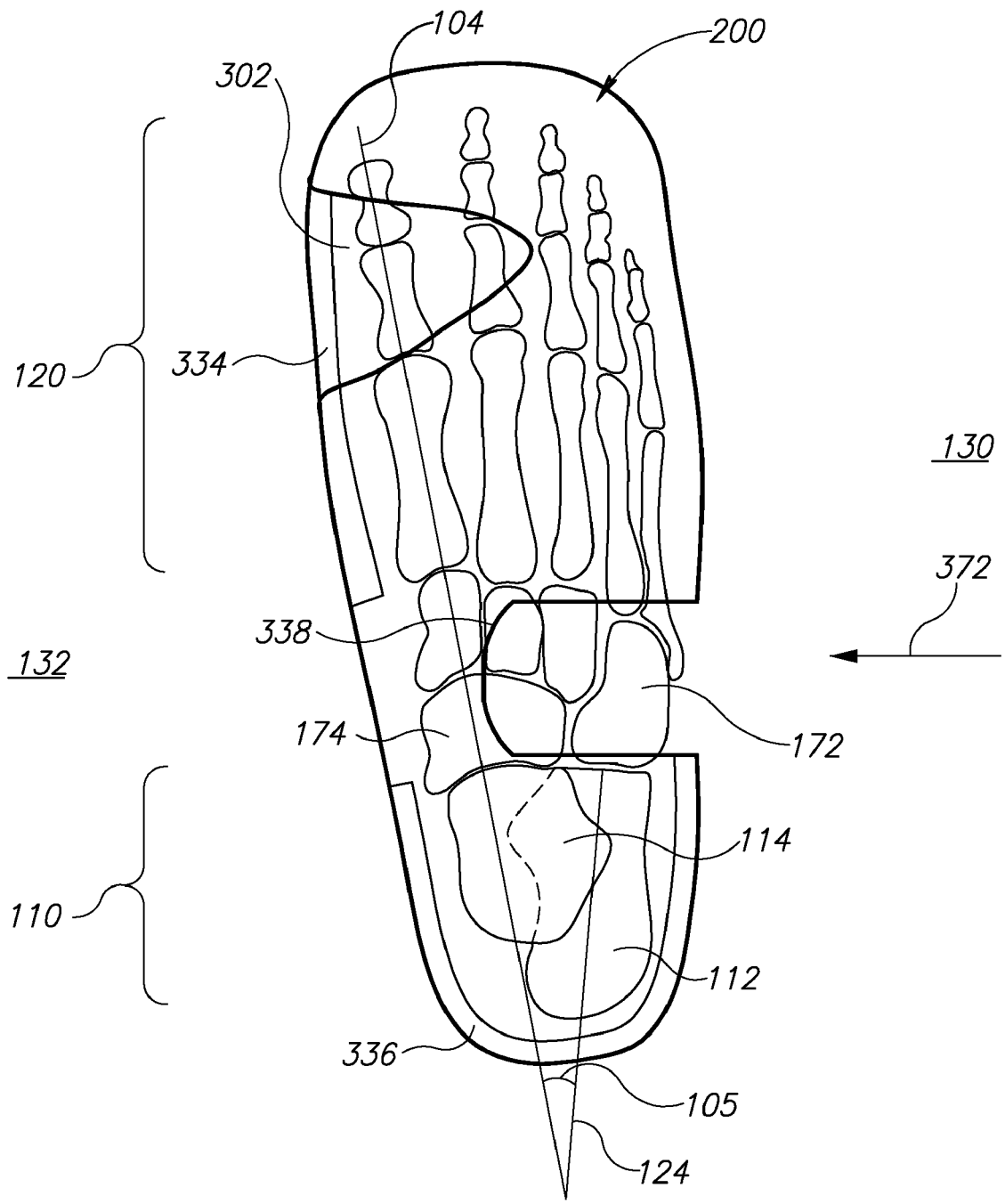

FIG. 12 shows a dorsal projection of the bones of clubfoot 200 demonstrating reduction of the angle between first ray axis 104 and calcaneal axis 124. Additionally, clubfoot orthotic 200 has created pressure in medial direction 133 to correct adductus of forefoot 120 and supinatus of first ray 104.

Correction of the above-noted components of clubfoot 200 is usually maintained (without clubfoot orthotic 300) following between at least about two weeks and four weeks of use of clubfoot orthotic 300. Following maintenance of the above-noted components, attention may be directed to correcting equines of rearfoot 110.

There are many methods and devices for treating the equinus component of clubfoot; the following equinus correction band being just one example; while just one other example will be explained further on.

Equinus Correction Band

Figure 13:
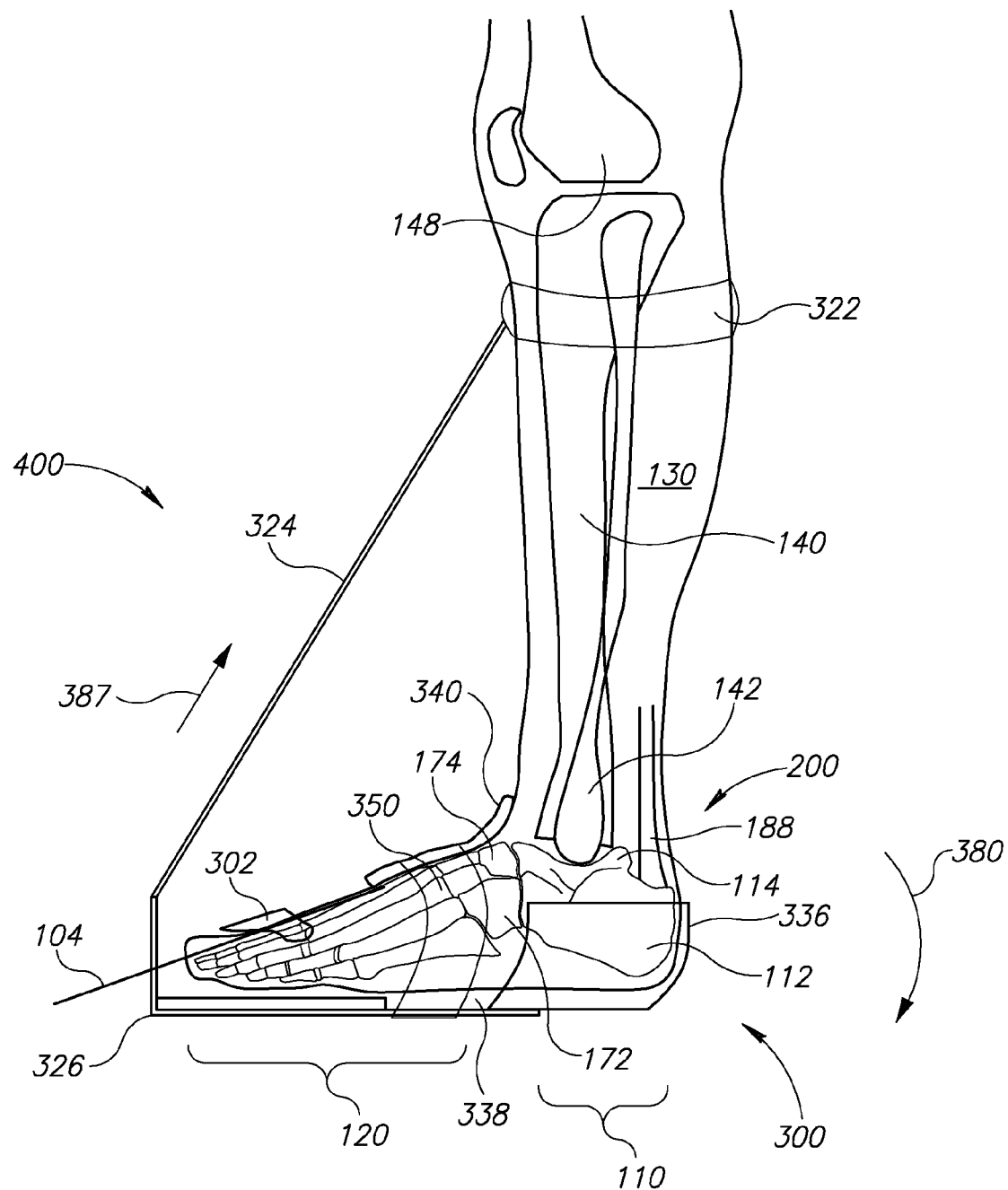

FIG. 13 shows a side view of clubfoot 200 and clubfoot orthotic 300, including an equinus corrector 400 comprising an orthotic connector 326 connected to the plantar aspect of the anterior of clubfoot orthotic 300.

A stretchable band 324 extending from orthotic connector 326 has been pulled in a substantially dorsal direction 387 and connected to a padded knee strap 322 that surrounds tibia 140 and fibula 142 below a knee joint 148. Stretchable band 324 pulls forefoot 120 dorsally, thereby gradually stretching an Achilles tendon 188, and/or a tibial posterior tendon (not shown) so that calcaneus 112 rotates in a plantigrade direction 380.

Stretchable band 324 is optionally connected lateral to the medial border of forefoot 120 in order to impart a valgus component to calcaneus 112 and assist in reversing varus of calcaneus 112.

In embodiments, stretchable band 324 is optionally connected near or along the lateral border of forefoot 120 to create an optimal corrective force on calcaneus 112.

Stretchable band 324 optionally comprises a stretchable rubber material and is optionally adjusted to apply tension to Achilles tendon 188 without causing discomfort to the infant.

Equinus corrector 400 is optionally used in conjunction with clubfoot orthotic 300 each night until Achilles tendon 188 maintains a stretched configuration without use of equinus corrector 400.

In embodiments Achilles tendon 188 maintains a stretched configuration following between about two and eight weeks of use of equinus corrector 400. In other embodiments, Achilles tendon 188 maintains a stretched configuration without equinus corrector 400 following between about four and six weeks of use of equinus corrector 400.

In the event of residual tightness of Achilles tendon 188, a surgical percutaneous Achilles tenotomy is optionally performed, thereby releasing the tightness. Optionally clubfoot orthotic 300 and equinus corrector 400 are used following the Achilles tenotomy in order to maintain the proper length of Achilles tendon 188.

After correction of Achilles tendon 188, clubfoot orthotic 300 and equinus corrector 400 are removed from corrected clubfoot 200.

Correction of equinus may be accomplished with alternative embodiments as noted above; the following equinus correction support being just one other, of many, examples.

Equinus Correction Support

Figure 14:
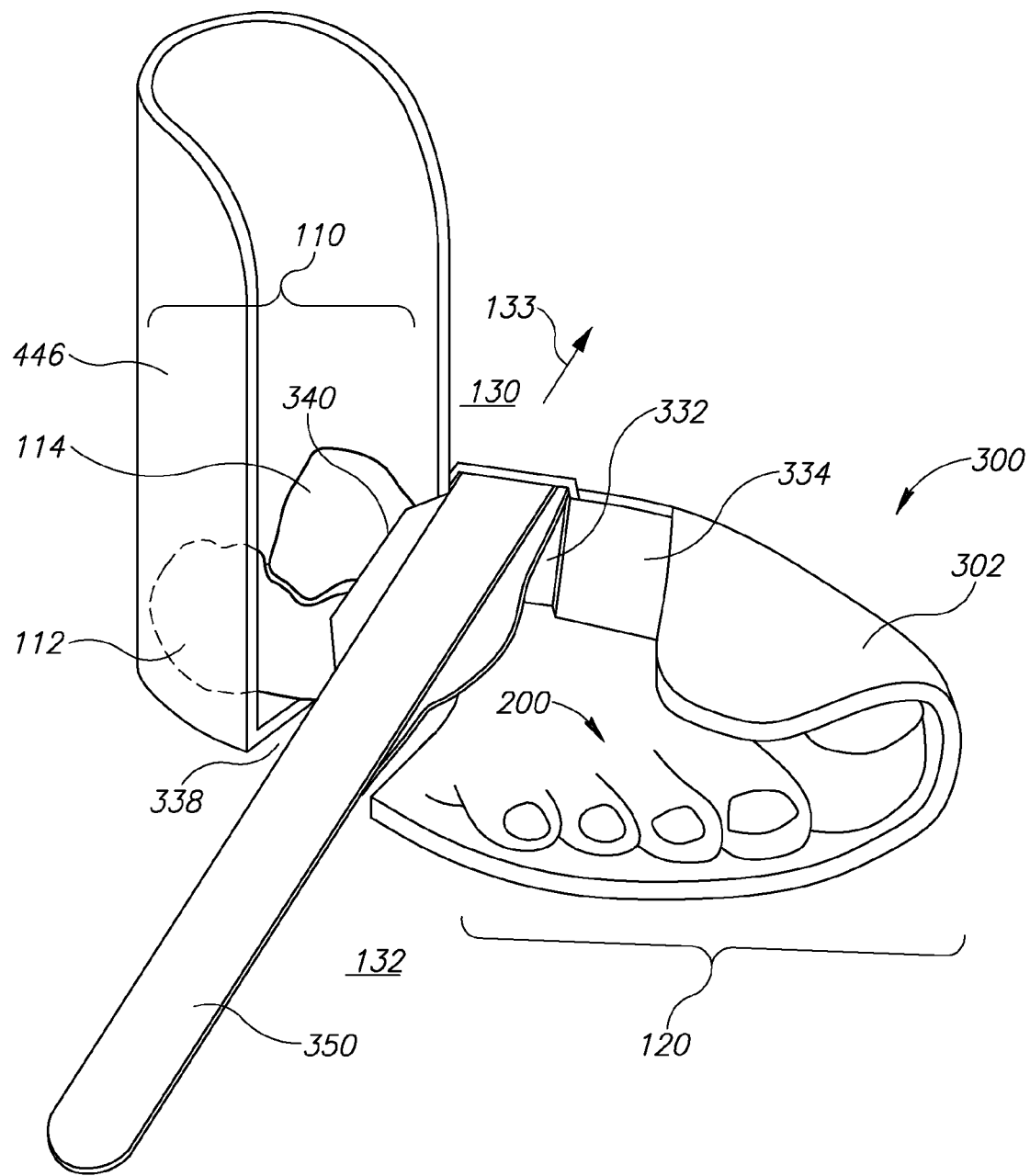

FIG. 14 shows right clubfoot 200 being strapped into clubfoot orthotic 300 having an elongate equinus correction support 446 that extends upward from clubfoot orthotic 300. Equinus correction support 446 is optionally flexible to allow dynamic stretching of the Achilles tendon so the foot is flexed to a 90 degree position with respect to the tibia, thereby dynamically providing correction of rearfoot equinus, as explained below.

Figure 15:
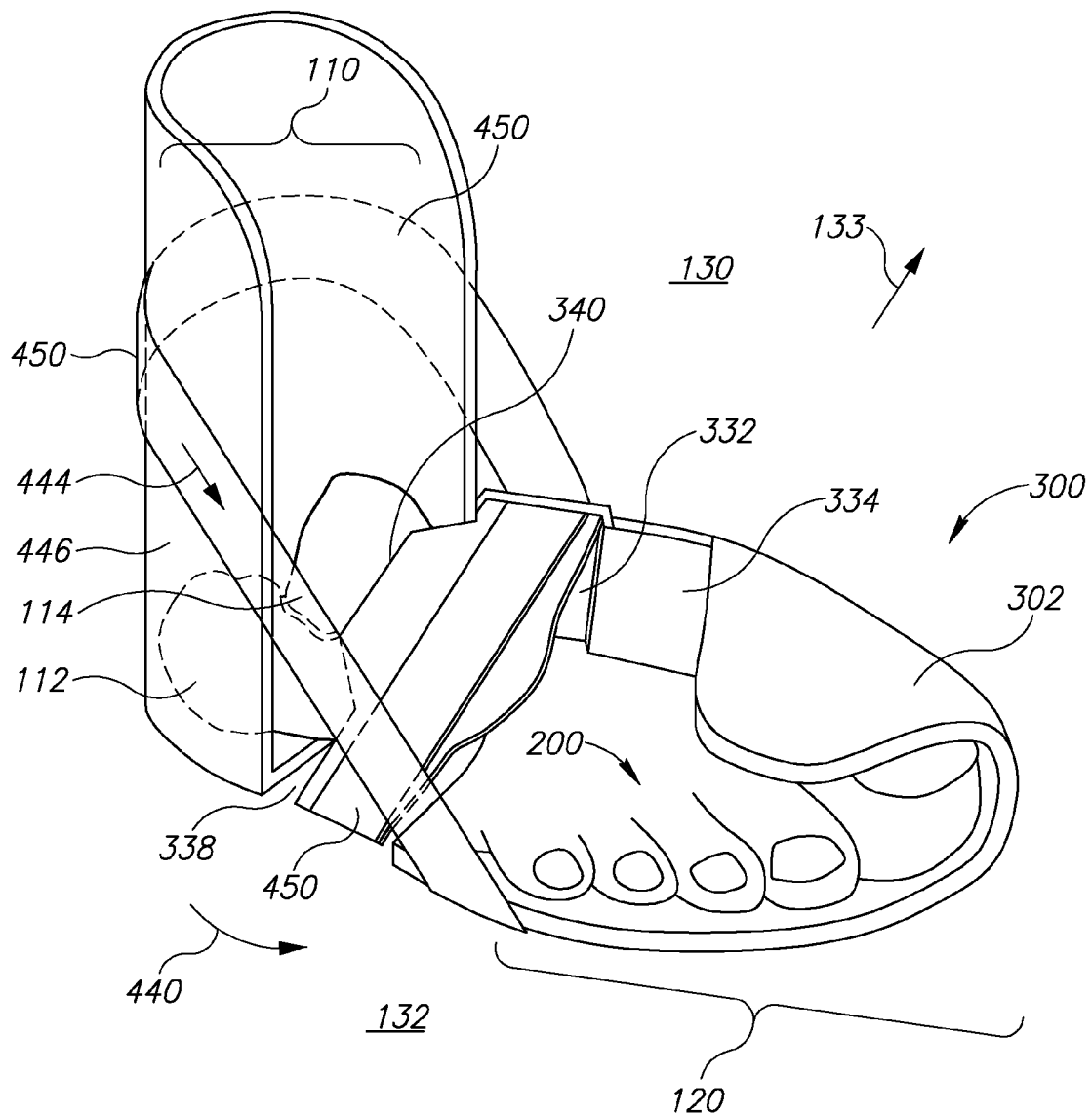

FIG. 15 shows right clubfoot 200 being strapped with an elongate stretchable strap 450 into clubfoot orthotic 300 having equinus correction support 446. As in previous Figures, elongate stretchable strap 450 is positioned over foot 200 and brought through subtalar sulcus 338, in a posterior direction 440.

Additionally, elongate stretchable strap 450 is tensioned in a posterior direction around equinus correction support 446 and then brought anteriorly in a direction 444 and secured on the plantar aspect of club foot orthotic 300, for example with a Velcro interface.

The continued stretch and relaxation of elongate stretchable strap 450 provides dynamic pressure on club foot 200 such that movement of clubfoot 200 causes the Achilles tendon to be gently pressed against equinus correction support 446. The dynamic pressure encourages clubfoot 200 to assume a 90 degree position with respect to the tibia, thereby dynamically stretching the Achilles tendon out of equinus.

In addition to encouraging elongation of the Achilles tendon, the inventor has found that elongate stretchable strap 450 may help to correct pes calcaneo varus (pronation forces) and internal tibial torsion (rotation forces).

The author has additionally found that some embodiments of the present invention may have advantages over U.S. Pat. No. 4,922,895 (Chong), (FIG. 4), noted above, who substantially addresses only the forefoot adductus component of clubfoot.

The author has additionally found that some embodiments of the present invention may have advantages over clubfoot treatments advocated by of Ignacio Ponseti, MD, noted above, in which the discomfortable straight-last shoes and transverse bar may result in non-compliance. Non-compliance is associated with a clubfoot relapse rate of 78%.

In distinct contrast to the Ponseti apparatus and method, the inventor has found that embodiments of the present clubfoot orthotic invention have not resulted in non-compliance; with the orthotic being substantially well tolerated by the infants.

It is expected that during the life of this patent many relevant materials and designs for clubfoot orthotic 300 will be developed and the scope of the term "clubfoot orthotic" is intended to include all such new technologies a priori.

As used herein the term "about" refers to ±10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An orthotic for treating clubfoot, comprising:
   an orthotic shell comprising a plantar support surface and a wall connected thereto, the plantar support comprising a lateral midfoot cutout and is arranged to support an anterior and a posterior parts of a foot disposed in the orthotic, and the wall comprising a midfoot portion medially supporting at least a part of the midfoot and a heel portion, and a strap having one end attached to the midfoot portion of the wall and having a length configured to contact at least a part of the midfoot dorsally and laterally, to apply on the midfoot a restoring force having a plantar component and a medial component, wherein the lateral midfoot cutout in the plantar surface is arranged to allow a movement of a cuboid of the foot in a plantar direction upon the application of the plantar component of the restoring force, to yield a proper alignment of the foot and a correction of the clubfoot deformity, and further comprising a clasp attached to a medial side of the midfoot portion of the wall and arranged to enable folding the strap backwards upon itself, wherein a second end of the strap is attachable upon a back of the strap, to apply the restoring force by passing the strap twice, over the clasp, dorsally and laterally over the midfoot.

2. An orthotic for treating clubfoot, comprising:

an orthotic shell comprising a plantar support surface and a wall connected thereto, the plantar support surface comprising a lateral midfoot cutout and is arranged to support an anterior and a posterior parts of a foot disposed in the orthotic, and the wall comprising a midfoot portion medially supporting at least a part of the midfoot and a heel portion, and a strap having one end attached to the midfoot portion of the wall and having a length configured to contact at least a part of the midfoot dorsally and laterally, to apply on the midfoot restoring force having a plantar component and a medial component, wherein the lateral midfoot cutout in the plantar surface is arranged to allow a movement of a cuboid of the foot in a plantar direction upon the application of the plantar component of the restoring force, to yield a proper alignment of the foot and a correction of the clubfoot deformity, and wherein the strap is padded at its dorsal and lateral contact area with the midfoot.

3. An orthotic for treating a clubfoot, comprising:

an orthotic shell comprising a plantar support surface and a wall connected thereto, the plantar support surface comprising a lateral midfoot cutout and is arranged to support an anterior and a posterior parts of a foot disposed in the orthotic, and the wall comprising a midfoot portion medially supporting at least a part of the midfoot and a heel portion, and a strap having one end attached to the midfoot portion of the wall and having a length configured to contact at least a part of the midfoot dorsally and laterally, to apply on the midfoot a restoring force having a plantar component and a medial component, wherein the lateral midfoot cutout in the plantar surface is arranged to allow a movement of a cuboid of the foot in a plantar direction upon the application of the plantar component of the restoring force, to yield a proper alignment of the foot and a correction of the clubfoot deformity, wherein the heel portion of the wall comprises an elongated Achilles support extending from a posterior aspect of the orthotic and configured to support a posterior aspect of the foot, and wherein the Achilles support has a flexible upper portion arranged to enable physiotherapeutic treatment to an ankle enclosed in the orthotic.

4. An orthotic for treating clubfoot, comprising:

an orthotic shell comprising a plantar support surface and a wall connected thereto, the plantar support surface comprising a lateral midfoot cutout and is arranged to support an anterior and a posterior parts of a foot disposed in the orthotic, and the wall comprising a midfoot portion medially supporting at least a part of the midfoot and a heel portion, and a strap having one end attached to the midfoot portion of the wall and having a length configured to contact at least a part of the midfoot dorsally and laterally, to apply on the midfoot a restoring force having a plantar component and a medial component, wherein the lateral midfoot cutout in the plantar surface is arranged to allow a movement of a cuboid of the foot in a plantar direction upon the application of the plantar component of the restoring force, to yield a proper alignment of the foot and a correction of the clubfoot deformity, wherein the heel portion of the wall comprises an elongated Achilles support extending from a posterior aspect of the orthotic and configured to support a posterior aspect of the foot, and further comprising a clasp attached to a medial side of the midfoot portion of the wall and arranged to enable folding the strap backwards, and wherein the strap is of sufficient length to pass posteriorly around the Achilles support and is attachable to an anterior plantar portion of the plantar support surface, to apply the restoring force by passing the strap twice, over the clasp, dorsally and laterally over the midfoot, as well as to apply a second restoring force over the Achilles support on a posterior part of the foot, wherein the plantar attachment of the strap enhances the second restoring force.

5. The orthotic of claim 4, wherein the strap is arranged to apply the second restoring force to pronate and externally rotate the foot, and wherein the Achilles support is arranged to allow movement of the ankle under the application of the second restoring force.

6. The orthotic of claim 5, further comprising a holder attached to the midfoot portion of the wall and arranged to hold the strap after passing back and forth through the clasp, and to fixate the strap to the midfoot before pass posteriorly around the Achilles support, to apply the two restoring forces independently of each other.

7. An orthotic for treating clubfoot, comprising:

an orthotic shell comprising a plantar support surface and a wall connected thereto, the plantar support surface comprising a lateral midfoot cutout and is arranged to support an anterior and a posterior parts of a foot disposed in the orthotic, and the wall comprising a midfoot portion medially supporting at least a part of the midfoot and a heel portion, and a strap having one end attached to the midfoot portion of the wall and having a length configured to contact at least a part of the midfoot dorsally and laterally, to apply on the midfoot a restoring force having a plantar component and a medial component, wherein the lateral midfoot cutout in the plantar surface is arranged to allow a movement of a cuboid of the foot in a plantar direction upon the application of the plantar component of the restoring force, to yield a proper alignment of the foot and a correction of the clubfoot deformity, wherein the wall comprises a first ray flange extending from at least a portion of the midfoot portion of the wall, and wherein at least a part of the wall is padded at a contact area with the foot.

8. A method of treating clubfoot, comprising:
supporting an anterior and a posterior plantar parts of a foot,
limiting a movement of a midfoot portion medially, while enabling movement of the midfoot portion in plantar and lateral directions, and
applying on the midfoot a restoring force having a plantar component and a medial component, to urge a movement of a cuboid of the foot in a plantar direction upon the application of the plantar component of the restoring force, to yield a proper alignment of the foot and a correction of the clubfoot deformity.

9. The method of claim 8, wherein the application of the restoring force on the midfoot is carried out by a strap.

10. The method of claim 8, further comprising applying a second restoring force to pronate and externally rotate the foot, to urge movement an ankle of the foot and the cuboid under the application of the second restoring force, to yield a proper alignment of the foot and a correction of the clubfoot deformity.

11. The method of claim 10, further comprising limiting a plantar flexion movement of the ankle while applying the second restoring force, to allow applying physiotherapy to the ankle.

12. The method of claim 10, wherein the application of both restoring forces is carried out by a single strap.

* * * * *